(12) United States Patent
Shi et al.

(10) Patent No.: US 12,357,375 B2
(45) Date of Patent: Jul. 15, 2025

(54) NASAL TURBINATE HEMOSTATIC ELECTRODE

(71) Applicant: BANGSHI MEDICAL TECHNOLOGY CO., LTD., Taizhou (CN)

(72) Inventors: Li Shi, Taizhou (CN); Xihua Huang, Taizhou (CN); Gang Peng, Taizhou (CN)

(73) Assignee: BANGSHI MEDICAL TECHNOLOGY CO. , LTD., Taizhou (CN)

( * ) Notice: Subject to any disclaimer, the term of this patent is extended or adjusted under 35 U.S.C. 154(b) by 0 days.

(21) Appl. No.: 18/863,669

(22) PCT Filed: Mar. 1, 2023

(86) PCT No.: PCT/CN2023/079089
§ 371 (c)(1),
(2) Date: Nov. 7, 2024

(87) PCT Pub. No.: WO2024/021602
PCT Pub. Date: Feb. 1, 2024

(65) Prior Publication Data
US 2025/0160931 A1    May 22, 2025

(30) Foreign Application Priority Data
Jul. 25, 2022 (CN) .......................... 202210878790.8

(51) Int. Cl.
*A61B 18/12* (2006.01)
*A61B 18/14* (2006.01)
*A61B 18/00* (2006.01)

(52) U.S. Cl.
CPC ..................... *A61B 18/1445* (2013.01); *A61B 2018/00327* (2013.01)

(58) Field of Classification Search
CPC .................. A61B 18/126; A61B 18/14; A61B 2018/00327; A61B 2018/00577; A61B 2018/1467; A61B 2218/001
See application file for complete search history.

(56) References Cited

U.S. PATENT DOCUMENTS

| 4,487,600 A | 12/1984 | Brownlie et al. |
| 2006/0259025 A1 | 11/2006 | Dahla |

(Continued)

FOREIGN PATENT DOCUMENTS

| CN | 105054991 A | 11/2015 |
| CN | 105407843 A | 3/2016 |

(Continued)

*Primary Examiner* — Daniel W Fowler
(74) *Attorney, Agent, or Firm* — Bayramoglu Law Offices LLC

(57) ABSTRACT

A nasal turbinate hemostatic electrode includes a main body, where an end of the main body is fixedly connected to a tip; the tip includes a first electrode and a second electrode; side walls of the first electrode and the second electrode are rounded; the first electrode and the second electrode are spaced apart, and have a same surface area; an end of the main body adjacent to the tip is provided with an outlet hole; the outlet hole is connected to an inlet pipe; the outlet hole is configured to deliver an electrolyte to the tip; and the first electrode and the second electrode are configured to conduct a plasma current in the electrolyte. The nasal turbinate hemostatic electrode prevents the surgical electrode from causing a secondary injury to the patient during an operation process, further improving the use safety of the surgical electrode.

6 Claims, 4 Drawing Sheets

(56) References Cited

U.S. PATENT DOCUMENTS

| | | | | |
|---|---|---|---|---|
| 2008/0161795 | A1* | 7/2008 | Wang | A61B 18/1492 606/41 |
| 2010/0160910 | A1* | 6/2010 | Kramer | A61B 18/1482 606/41 |
| 2012/0029506 | A1 | 2/2012 | Johnson | |
| 2014/0200581 | A1* | 7/2014 | Aluru | A61B 18/14 606/41 |
| 2016/0135880 | A1* | 5/2016 | Ellman | A61B 18/148 606/41 |

FOREIGN PATENT DOCUMENTS

| | | |
|---|---|---|
| CN | 205360078 U | 7/2016 |
| CN | 106308929 A | 1/2017 |
| CN | 108143481 A | 6/2018 |
| CN | 109621020 A | 4/2019 |
| CN | 109953815 A | 7/2019 |
| CN | 110464452 A | 11/2019 |
| CN | 209751759 U | 12/2019 |
| CN | 210205444 U | 3/2020 |
| CN | 111388084 A | 7/2020 |
| CN | 112022341 A | 12/2020 |
| CN | 112842518 A | 5/2021 |
| CN | 112869874 A | 6/2021 |
| CN | 216319125 U | 4/2022 |
| CN | 115252114 A | 11/2022 |
| JP | 2020005875 A | 1/2020 |
| WO | 2018006383 A1 | 1/2018 |

* cited by examiner

NASAL TURBINATE HEMOSTATIC ELECTRODE

CROSS REFERENCE TO THE RELATED APPLICATIONS

This application is the national phase entry of International Application No. PCT/CN2023/079089, filed on Mar. 1, 2023, which is based upon and claims priority to Chinese Patent Application No. 202210878790.8, filed on Jul. 25, 2022, the entire contents of which are incorporated herein by reference.

TECHNICAL FIELD

The present disclosure belongs to the technical field of medical instruments, and in particular to a nasal turbinate hemostatic electrode.

BACKGROUND

In gas discharge research of the 1830s, humans began to understand plasma systems and established the concept of plasma in the early $20^{th}$ century, which is a macroscopic spatiotemporal scale system composed of a large number of specific interacting charged particles. Plasma is divided into high-temperature plasma and low-temperature plasma according to the temperature of charged particles. Among them, the low-temperature plasma refers to ionized, electrically neutral gases, which is a form of material existence, also known as the fourth state.

Low-temperature plasma technology is a relatively mature and flourishing applied science, which has been widely applied in the fields of traditional and high-temperature technologies. At the beginning of the $21^{st}$ century, low-temperature plasma radiofrequency was used in electrical surgery, gradually demonstrating various advantages. In the plasma radiofrequency technology, the energy generated by bipolar radiofrequency converts the electrolyte between the radiofrequency tip and the tissue into a thin layer of plasma. Charged particles in the plasma are accelerated by an electric field and transfer energy to the tissue to dissociate molecular bonds that make up cellular molecules in the target tissue. The cells in the target tissue decompose into carbohydrates and oxides in molecular units, causing coagulation necrosis of the tissue, shedding of the necrotic tissue or the formation of cicatricial contraction, resulting in a tissue volume reduction or cutting effect. Compared with ordinary radiofrequency technology, in the plasma radiofrequency technology, the plasma carries out surgical procedures such as cutting and ablation of tissues at lower temperatures (40-70° C.) at lower radio frequencies (100 KHz). This avoids the process such as cutting, ablation, and hemostasis through the heating effect caused by molecular friction in the ordinary radiofrequency technology, thereby reducing thermal damage to tissues and achieving a minimally invasive effect.

At present, plasma technology is applied in turbinate related surgeries for turbinate ablation, hemostasis and debridement through different tips. The existing plasma electrodes are mostly coagulate-while-cut electrodes, which pursue discharge tips that are fine enough for cutting and pursue good hemostatic effects. However, these two goals cannot be achieved simultaneously, and sometimes there are even secondary injuries caused by the coagulate-while-cut procedure.

Therefore, it is highly desirable for those skilled in the art to develop a low-temperature plasma electrode device with a simple structure, convenient operation, minimal trauma, high safety, and good hemostatic effect for minimally invasive treatment of surgical procedures.

SUMMARY

In response to the above-mentioned shortcomings of the prior art, the present disclosure provides a nasal turbinate hemostatic electrode. The present disclosure solves the technical problems that a surgical electrode in the prior art is likely to cause a secondary injury and its safety needs to be improved.

In order to achieve the above objective, the present disclosure adopts the following technical solution:

A nasal turbinate hemostatic electrode includes a main body, where an end of the main body is fixedly connected to a tip;

the tip includes a first electrode and a second electrode; and side walls of the first electrode and the second electrode are rounded;

the first electrode and the second electrode are spaced apart, and have a same surface area; and an end of the main body adjacent to the tip is provided with an outlet hole; the outlet hole is connected to an inlet pipe; the outlet hole is configured to discharge an electrolyte from the tip; and the first electrode and the second electrode are configured to conduct a plasma current in the electrolyte.

In the above solution of the present disclosure, a segmented electrode structure is adopted, specifically including the first electrode and the second electrode. Through this method, both the positive and negative electrodes of the surgical electrode are arranged at the end of the tip to form a symmetrical structure. The rounded side walls of the electrodes avoid technical defects in traditional techniques. That is, when a single electrode is exposed and its edge touches a patient's nasal cavity, it will cause a scratch and secondary injury to the nasal cavity. As mentioned earlier, in the present disclosure, the symmetrical structure is formed between the positive electrode and the negative electrode. In this way, no matter which side of the tip comes into contact with the nasal cavity after entering the work area, it will not cause scratching. For this purpose, the sidewalls of the first electrode and the second electrode are rounded, further improving the use safety of the device.

Further, ends of the first electrode and the second electrode are fixedly connected to an insulating head; the insulating head is sleeved outside the tip; an insulating sheet is fixedly provided in a middle portion of the insulating head; and the insulating sheet is located between the first electrode and the second electrode.

In the above solution, the insulating sheet is located between the first electrode and the second electrode, and the insulating sheet has two functions. First, the insulating sheet prevents a short circuit between the first electrode and the second electrode, thereby preventing device damage. Second, the insulating sheet fills in the gap between the first electrode and the second electrode to avoid the risk of scratching the nasal cavity due to the formation of a sharp edge in the gap. The above structure effectively improves the operational stability of the device and further enhances the use safety of the device.

Further, the side wall of the tip is provided with a suction hole; the suction hole is connected to a through pipe; the suction hole is configured to recover a tissue cut by the tip; and a side of the suction hole is provided with an opening control device.

In the above solution, the suction hole on the side wall of the tip can carry out centralized suction and recovery of the tissue cut by the first electrode and the second electrode. This solution can maintain the cleanliness of the operating area of the device, and avoid excessive accumulation of the cut tissue in the nasal cavity, which will cause clogging and affect the cutting process.

Further, the main body includes a shank; one end of the shank is connected to the tip, and the other end of the shank is connected to a handle; and the insulating head is inserted at an end portion of the shank.

the shank is a hollow structure, and the outlet hole is provided on a side wall of the shank.

In the above solution, the electrolyte can be discharged from the shank through the outlet hole. This structure facilitates the discharge of electrolyte from the tip and facilitates the tissue cutting work.

Further, there are a plurality of suction holes; and the plurality of suction holes are located at a side of the first electrode or a side of the second electrode.

The above solution can handle the clogging problem of the suction hole caused by a cut tissue with an excessive diameter or a plurality of cut tissues entering the suction hole simultaneously during the cutting and hemostasis process of the device. If a suction hole is clogged by a cut tissue, the remaining cut tissue can be discharged from the nasal cavity through another suction hole. This solution improves the fault tolerance of the device, and can still complete the discharge of the cut tissue in the event of a clogging or malfunction in one of the suction holes.

Further, the through pipe is connected to a negative pressure pipe, and the negative pressure pipe extends out of a tail of the main body.

Further, the through pipe is made of a conductive material, and an end of the through pipe is connected to a power cable.

In the above solution, the electricity is conducted to the through pipe such that an electric field is generated between the first electrode and the second electrode, allowing charged particles in the electrolyte to complete the cutting of the tissue inside the nasal cavity. This structure avoids the need to provide a cable in the tip to power the first electrode and the second electrode. The through pipe plays a dual role as a conductive component and an electrolyte conduit, simplifying the circuit layout inside the tip and reducing preparation costs.

Further, the opening control device includes a sealing head; an end of the sealing head is rotatably connected to a screw rod; a side of the screw rod is threaded to a fixed element; and the fixed element is fixedly provided on an inner wall of the tip; and an end of the screw rod is connected in a transmission manner to a transmission component; the transmission component is connected to a micro motor; the micro motor is configured to transmit a torque to the screw rod through the transmission component; and the micro motor is slidably connected inside the tip.

In the above solution, the screw rod is rotatably driven, without the need to provide an excessively long rod in the narrow space of the tip, thereby improving the movement stability of the sealing head.

Further, the transmission component includes a first gear; an output shaft of the micro motor is fixedly connected at an axis of the first gear; the first gear is meshed with a second gear; and the screw rod is fixedly connected at an axis of the second gear.

In summary, the present disclosure has the following beneficial effects.

1. The present disclosure effectively avoids scratches and secondary injuries caused by the surgical electrode during the cutting and hemostasis process through the symmetrically arranged segmented electrodes.
2. The present disclosure provides the insulating element between the two electrodes to fill an edge-occurring position in the tip, thereby preventing a short circuit between the two electrodes and further improving the use safety of the tip while completing basic cutting work.
3. The present disclosure provides the opening control device at the side of the suction hole to avoid dust accumulation and clogging during storage of the device. When in use, if a suction hole is clogged, the sealing head can be repeatedly moved to crush large particles into small particles that are easy to suck out. This solution further reduces the risk of clogging the suction hole.

Figure 1:
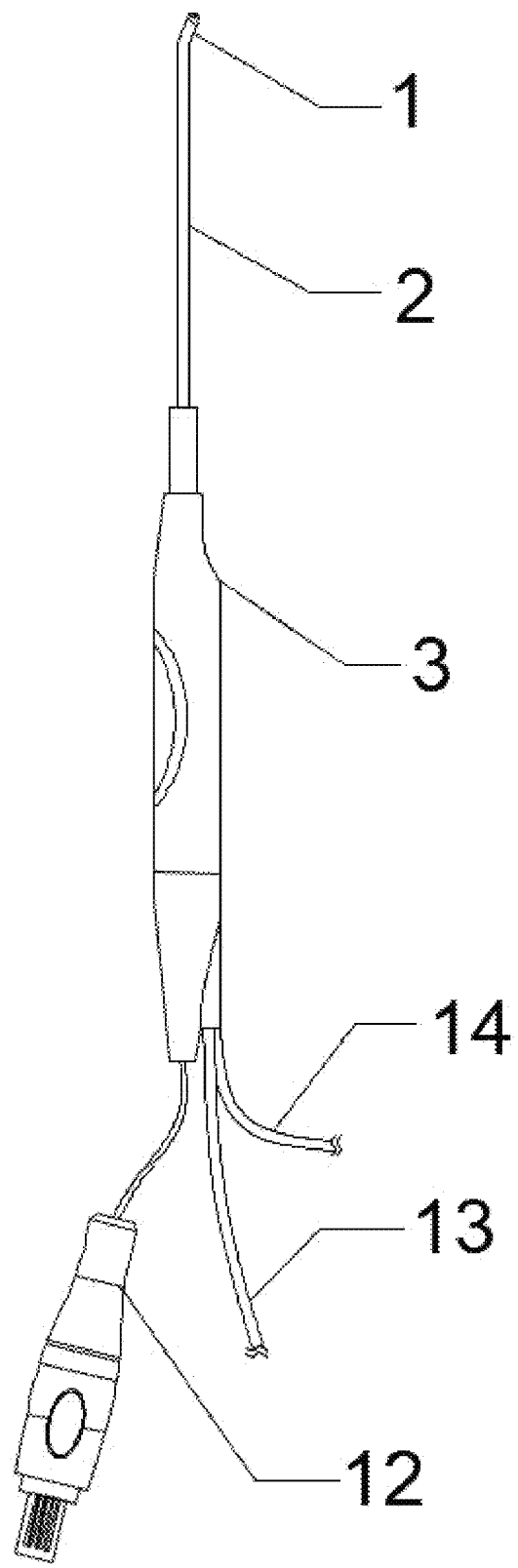
FIG. 1 is a lateral view of a nasal turbinate hemostatic electrode according to the present disclosure.

Reference Numerals: 1. tip; 2. shank; 3. main body; 5. first electrode; 6. second electrode; 7. insulating head; 8. suction hole; 9. through pipe; 10. insulating layer; 11. outlet hole; 12. power cable; 13. negative pressure pipe; 14. inlet pipe; 15. fixed element; 16. sealing head; 17. screw rod; 18. transmission component; 19. micro motor; 20. first gear; 21. second gear; and 22. bearing.

DETAILED DESCRIPTION OF THE EMBODIMENTS

The specific embodiment of the present disclosure will be described below so that those skilled in the art can understand the present disclosure, but it should be clear that the present disclosure is not limited to the scope of the specific embodiment. For those of ordinary skill in the art, as long as various changes fall within the spirit and scope of the present disclosure defined and determined by the appended claims, these changes are apparent, and all inventions and creations using the concept of the present disclosure are protected.

Embodiment 1

A nasal turbinate hemostatic electrode includes main body 3. An end of the main body 3 is fixedly connected to tip 1.

The tip 1 includes first electrode 5 and second electrode 6. Side walls of the first electrode 5 and the second electrode 6 are rounded.

The first electrode 5 and the second electrode 6 are spaced apart, and have a same surface area.

An end of the main body 3 adjacent to the tip 1 is provided with outlet hole 11. The outlet hole 11 is connected to inlet pipe 14. The outlet hole 11 is configured to discharge an electrolyte from the tip 1, and the first electrode 5 and the second electrode 6 are configured to conduct a plasma current in the electrolyte.

In the above embodiment, the tip 1 includes the first electrode 5 and the second electrode 6, which operate based on the following principle. After the first electrode 5 and the second electrode 6 are energized, they emit a radiofrequency and generate energy. Charged particles in the electrolyte are accelerated and transfer the energy to a tissue to complete tissue cutting and hemostasis. The first electrode 5 and the second electrode 6 are symmetrical to each other. Through this symmetrical structure, the tip 1 avoids sharp edges in any direction, thereby avoiding scratches after entering a nasal cavity.

Figure 2:
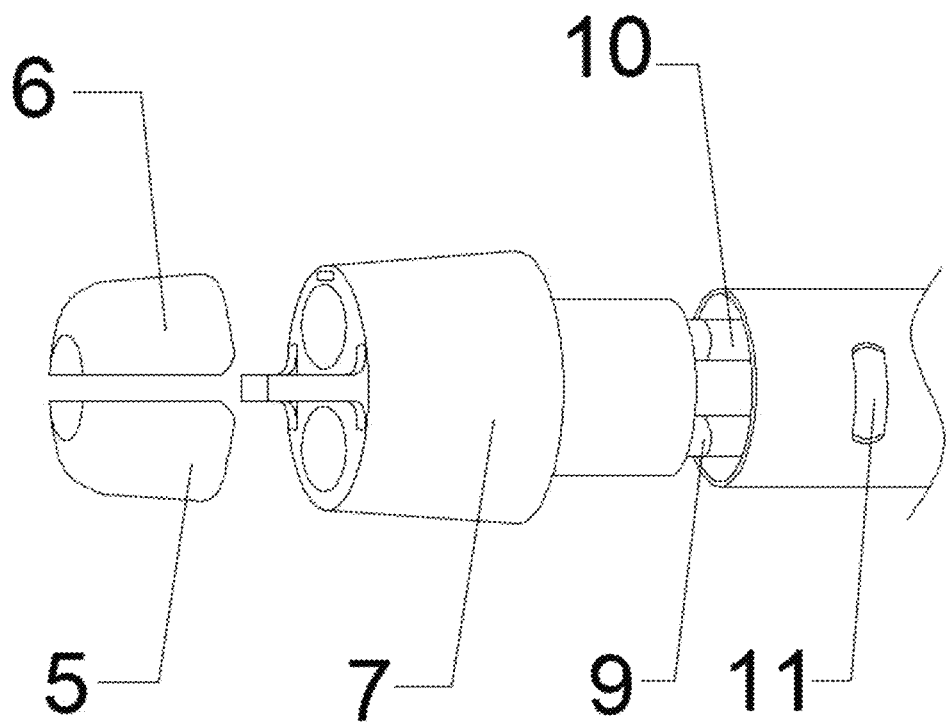
FIG. 2 is a structural diagram of a tip according to the present disclosure.
Figure 3:
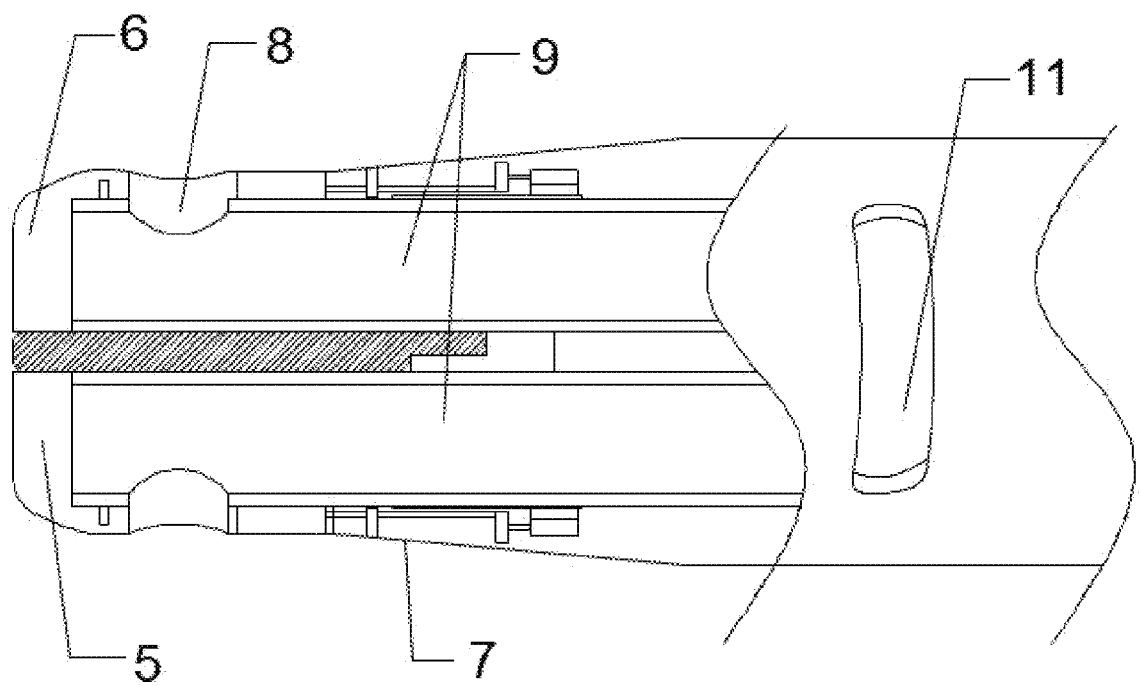
FIG. 3 is a section view of the tip according to the present disclosure.
Figure 4:
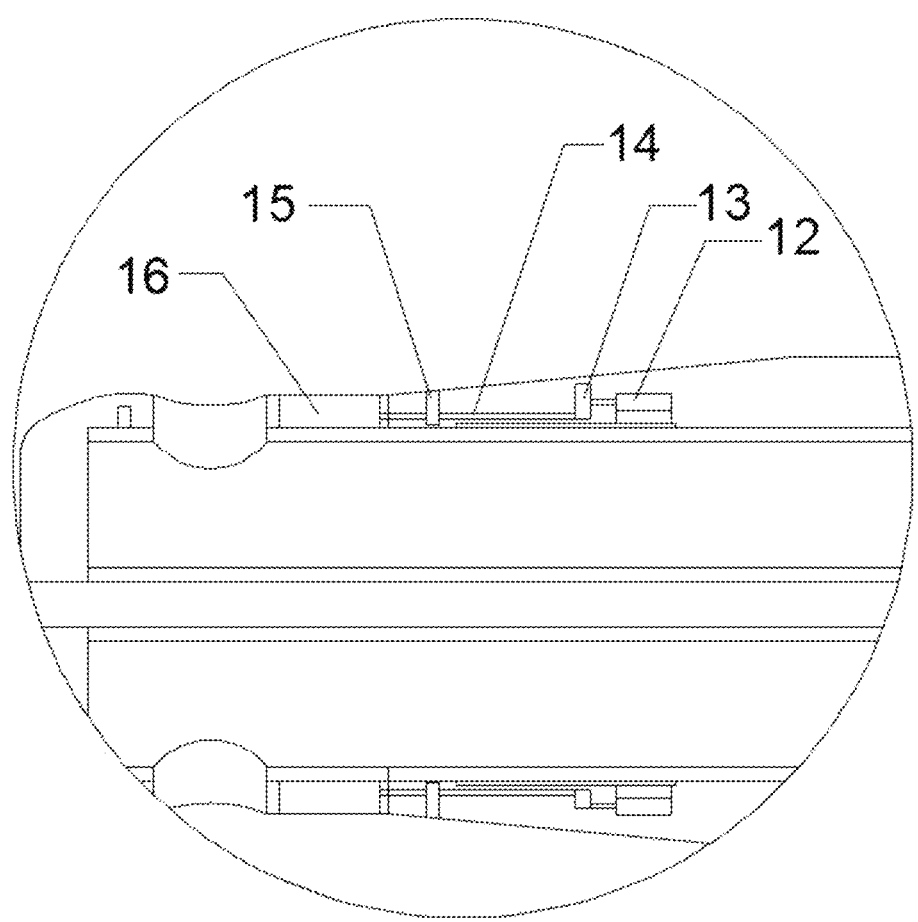
FIG. 4 is a schematic diagram of an opening control device according to the present invention.

Furthermore, the side walls of the first electrode 5 and the second electrode 6 are rounded. The side walls of the second electrode 5 and the second electrode 6 are arc-shaped structures. The arc-shaped structure protrudes outward away from an axis of the tip 1. Through this structure, the first electrode 5 and the second electrode 6 form a hemispherical structure, as shown in FIG. 2. When the hemispherical structure contacts an inner wall of the nasal cavity, due to its smooth surface, the hemispherical structure will not cause excessive pressure at a certain point of the tip 1, thereby avoiding damage to the nasal cavity. In addition, the arc-shaped structure of the tip 1 further enhances the use safety of the device.

In the above solution, the first electrode 5 and the second electrode 6 have the same surface area. Through this solution, the current is formed between the first electrode 5 and the second electrode 6, enhancing the cutting accuracy of the device.

The first electrode 5 and the second electrode 6 cannot come into direct contact. To avoid a short circuit fault, ends of the first electrode 5 and the second electrode 6 are fixedly connected to insulating head 7. The insulating head 7 is sleeved outside the tip 1. An insulating sheet is fixedly provided in a middle portion of the insulating head 7. The insulating sheet is located between the first electrode 5 and the second electrode 6.

The main body 3 includes shank 2. One end of the shank 2 is connected to the tip 1, and the other end of the shank 2 is connected to a handle. The insulating head 7 is inserted at an end portion of the shank 2.

In this embodiment, the structure of the insulating head 7 is shown in FIG. 2. The middle portion of the insulating head 7 is provided with the insulating sheet. The insulating sheet divides an interior of the insulating head 7 into two cavities. The first electrode 5 and the second electrode 6 extend out of the insulating head 7 through the two cavities, respectively.

An end of the insulating head 7 away from the tip 1 is provided with a clamp. The clamp is a cylindrical structure that is clamped in the shank 2, forming a clamping fixation on the shank 2.

As mentioned earlier, the first electrode 5 and the second electrode 6 require the electrolyte to cut a nasal tissue. In this embodiment, the electrolyte is delivered through the shank 2. Specifically, the shank 2 is a hollow structure, and the outlet hole 11 is provided on a side wall of the shank 2. In the above solution, the shank 2 is a hollow structure, considering that the dual electrodes of this device need to work in an electrolyte environment and the internal conduits of the shank 2 need to be optimized. Due to the hollow structure of the shank 2, the electrolyte flows in a hollow cavity of the shank 2 and is discharged from the outlet hole 11. The design avoids adding an electrolyte conduit in the shank 2, thereby avoiding crowded and complex conduit arrangements inside the shank 2.

After the two electrodes of the tip 1 cut the tissue, the cut tissue stays in an operating area of the tip 1. In view of this, a side wall of the tip 1 is provided with suction hole 8. The suction hole 8 is connected to through pipe 9. The suction hole 8 is configured to recover a tissue cut by the tip 1. In the above solution, the suction hole 8 can suck the cut tissue into the through pipe 9, avoiding the tissue accumulating in the operating area of the tip 1.

The difference between the suction hole 8 of the present disclosure and the prior art is as follows. The suction hole 8 in the present disclosure is located at a side of the tip 1, and this structure is adapted to the symmetrical electrode structure of the present disclosure.

Specifically, the first electrode 5 and the second electrode 6 form a symmetrical structure, and an insulating element is provided between the two electrodes. Therefore, the suction hole 8 is provided at the side of the tip 1. The suction hole 8 provided at the side of tip 1 is not limited by the arc-shaped structure of the tip 1. During preparation, the diameter of the suction hole 8 is adjustable according to actual usage needs. If the suction hole 8 is located at a top of the tip 1, a maximum diameter of the suction hole 8 can only be a width of a top of the first electrode 5 or the second electrode 6, which is relatively limited.

Furthermore, there are a plurality of suction holes 8. The plurality of suction holes 8 are located at a side of the first electrode 5 or a side of the second electrode 6.

In the above solution, the plurality of suction holes 8 are designed to reduce the failure rate of this device. In case one of the suction holes 8 is clogged, the remaining suction holes 8 can continue to perform the suction work. The design avoids the technical defect of traditional technology where the suction work cannot be continued when the single suction hole 8 is clogged. In this embodiment, there are two suction holes 8 located at the side of the first electrode 5 and the side of the second electrode 6, respectively.

The through pipe 9 is made of a conductive material; and an end of the through pipe 9 is connected to power cable 12.

In the above solution, the through pipe 9 serves as both a suction pathway and a conductive element. During use, the power cable 12 conducts electricity to the through pipe 9, and the through pipe 9 charges the first electrode 5 and the second electrode 6 to perform tissue cutting work. Meanwhile, the suction holes 8 suck the cut tissue into the through pipe 9, and the through pipe 9 discharges the cut tissue from the main body 3. In the above solution, the electrification function and the suction hole 8 connection function are integrated into the through pipe 9, simplifying the internal conduit layout of the shank 2 and the tip 1 and reducing the preparation cost. Furthermore, insulating layer 10 is sleeved outside the through pipe 9 to prevent the current from leaking into the electrolyte to damage the device.

Furthermore, opening control device includes sealing head 16. An end of the sealing head 16 is rotatably connected to screw rod 17. A side of the screw rod 17 is threaded to fixed element 15. The fixed element 15 is fixedly provided on an inner wall of the tip 1.

An end of the screw rod 17 is connected in a transmission manner to transmission component 18. The transmission component 18 is connected to micro motor 19. The micro motor 19 is configured to transmit a torque to the screw rod 17 through the transmission component 18. The micro motor 19 is slidably connected inside the tip 1.

In the above solution, there is a cavity inside the tip 1. The opening control device is provided inside the cavity. The opening control device includes the sealing head 16. The sealing head 16 is movable in a straight direction and able to open and close the suction holes 8 during the movement. When the sealing head 16 completely covers the suction holes 8, the sealing of the suction holes 8 is completed. When this device is stored, the suction holes 8 are sealed with the sealing head 16 to prevent dust. When the suction hole 8 is clogged, it can be repeatedly opened and closed by the sealing head 16, such that the large particles at the suction hole 8 are crushed into small particles that can be smoothly sucked.

The sealing head 16 moves back and forth through the screw rod 17. Specifically, the screw rod 17 is threaded to the fixed element 15. When the screw rod 17 rotates, it can move in a straight direction with the fixed element under the action of thread rotation. The screw rod 17 is driven by the micro motor 19 to rotate. An output shaft of the micro motor 19 transmits the torque to the screw rod 17 through the transmission component 18. The micro motor 19 is slidably connected to the tip 1. When the screw rod 17 moves back and forth, the micro motor moves back and forth under the drive of the screw rod 17. Furthermore, a slide rail is provided in the internal cavity of the tip 1, and a slider is fixedly provided at a bottom of the micro motor 19. The slider is slidable in the slide rail. Through this solution, the micro motor 19 is slidably connected to the tip 1. In other solutions, a moving wheel may be provided at the bottom of the micro motor 19. Through this solution, the micro motor 19 is slidably connected to the tip 1.

Furthermore, a second bearing is provided at an end of the sealing head 16. An outer wall of the second bearing is fixedly connected to the sealing head 16. An inner wall of the second bearing is fixedly connected to the screw rod 17. The inner wall and the outer wall of the second bearing can rotate relative to each other. Through this solution, the sealing head 16 is rotatably connected to the screw rod 17.

Figure 5:
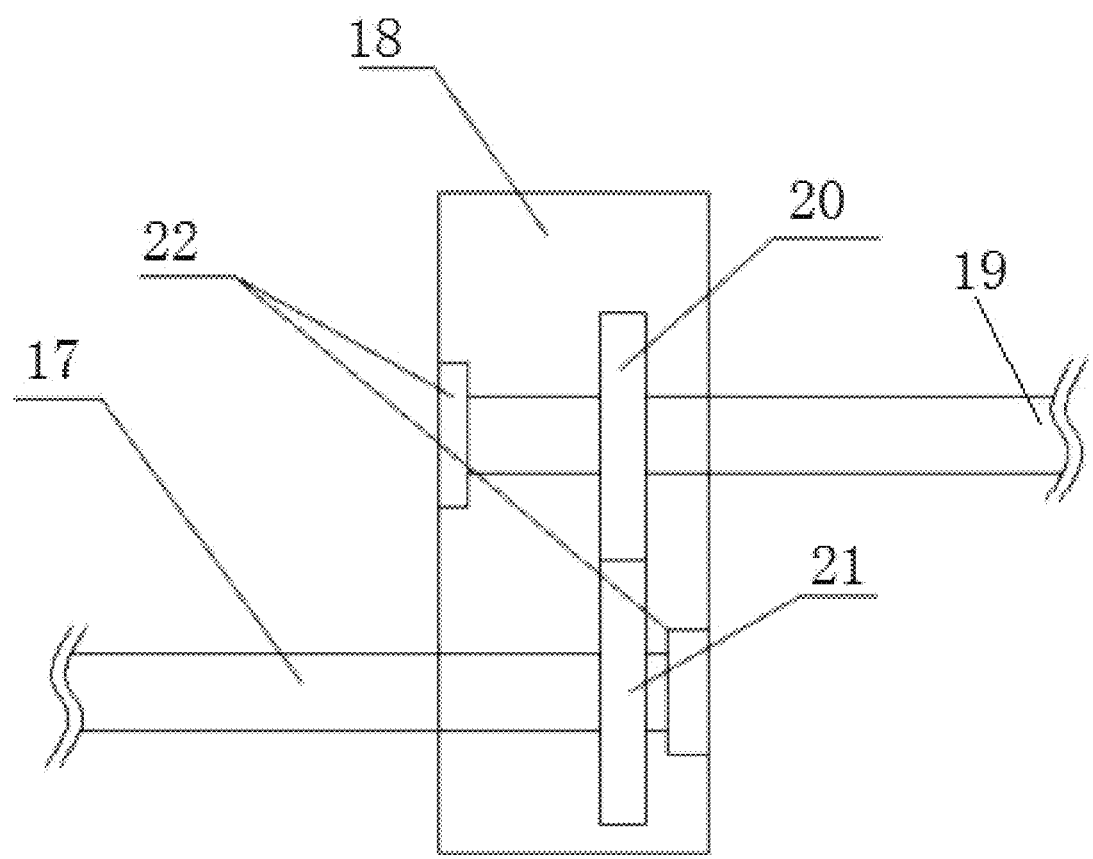
FIG. 5 is a schematic diagram of a power unit according to the present invention.

The transmission component 18 includes first gear 20. The output shaft of the micro motor 19 is fixedly connected at an axis of the first gear 20. The first gear 20 is meshed with second gear 21. The screw rod 17 is fixedly connected at an axis of the second gear 21. When the output shaft of the micro motor 19 rotates, it drives the first gear 20 to rotate. Since the first gear 20 is meshed with the second gear 21, the second gear 21 can rotate at a same linear speed under the drive of the first gear 20 and drive the screw rod 17 to rotate. The specific structure is shown in FIG. 5. The transmission component 18 has a box structure. To ensure the rotational stability of the output shaft of the micro motor 19 and the screw rod 17, two bearings 22 are provided inside the transmission component 18. Among them, one bearing 22 is connected to the output shaft of the micro motor 19, and the other bearing 22 is connected to the screw rod 17. Through this solution, the output shaft of the micro motor 19 and the screw rod 17 are fixed at two points, improving rotational stability.

What is claimed is:

1. A nasal turbinate hemostatic electrode, comprising a main body, wherein an end of the main body is fixedly connected to a tip;
   the tip comprises a first electrode and a second electrode, wherein the first electrode and the second electrode are symmetrically arranged; and side walls of the first electrode and the second electrode are rounded;
   the first electrode and the second electrode are spaced apart, and have a same surface area;
   an end of the main body adjacent to the tip is provided with an outlet hole; the outlet hole is connected to an inlet pipe; the outlet hole is configured to discharge an electrolyte from the tip; and the first electrode and the second electrode are configured to conduct a plasma current in the electrolyte;
   ends of the first electrode and the second electrode are fixedly connected to an insulating head; the insulating head is sleeved outside the tip; an insulating sheet is fixedly provided in a middle portion of the insulating head; and the insulating sheet is located between the first electrode and the second electrode;
   a side wall of the tip is provided with a suction hole; the suction hole is connected to a through pipe; the suction hole is configured to recover a tissue cut by the tip; and a side of the suction hole is provided with an opening control device;
   the opening control device comprises a sealing head; an end of the sealing head is rotatably connected to a screw rod; a side of the screw rod is threaded to a fixed element; and the fixed element is fixedly provided on an inner wall of the tip;
   an end of the screw rod is connected to a transmission component; the transmission component is connected to a micro motor; the micro motor is configured to transmit a torque to the screw rod through the transmission component; and the micro motor is slidably connected inside the tip; and
   the through pipe is made of a conductive material, an end of the through pipe is connected to a power cable, and an insulating layer is sleeved outside the through pipe.

2. The nasal turbinate hemostatic electrode according to claim 1, wherein the main body comprises a shank; a first end of the shank is connected to the tip, and a second end of the shank is connected to a handle; and the insulating head is inserted at the first end of the shank.

3. The nasal turbinate hemostatic electrode according to claim 1, wherein the shank is a hollow structure, and the outlet hole is provided on a side wall of the shank.

4. The nasal turbinate hemostatic electrode according to claim 1, wherein a plurality of suction holes are provided at a side of the first electrode or a side of the second electrode.

5. The nasal turbinate hemostatic electrode according to claim 1, wherein the through pipe is connected to a negative pressure pipe, and the negative pressure pipe extends out of a tail of the main body.

6. The nasal turbinate hemostatic electrode according to claim 1, wherein the transmission component comprises a first gear; an output shaft of the micro motor is fixedly connected at an axis of the first gear; the first gear is meshed with a second gear; and the screw rod is fixedly connected at an axis of the second gear.

* * * * *